(12) United States Patent
Zhao et al.

(10) Patent No.: US 10,603,194 B2
(45) Date of Patent: Mar. 31, 2020

(54) CLOSE-CELL STRUCTURED STENT, A PREPARATION METHOD AND USE THEREOF

(71) Applicant: Beijing Advanced Medical Technologies, Ltd. Inc., Beijing (CN)

(72) Inventors: Hugh Qinghong Zhao, Pleasanton, CA (US); Guixin Shi, Boucherville (CA); Yongquan Gu, Beijing (CN); Qing Liu, Beijing (CN)

(73) Assignee: Beijing Advanced Medical Technologies, Ltd. Inc., Beijing (CN)

( * ) Notice: Subject to any disclaimer, the term of this patent is extended or adjusted under 35 U.S.C. 154(b) by 0 days.

(21) Appl. No.: 15/837,445

(22) Filed: Dec. 11, 2017

(65) Prior Publication Data

US 2018/0104044 A1    Apr. 19, 2018

Related U.S. Application Data

(63) Continuation of application No. PCT/CN2015/081216, filed on Jun. 11, 2015.

(51) Int. Cl.
*A61F 2/915*    (2013.01)
*A61F 2/90*    (2013.01)
(Continued)

(52) U.S. Cl.
CPC ............... *A61F 2/915* (2013.01); *A61F 2/07* (2013.01); *A61F 2/90* (2013.01); *A61F 2/91* (2013.01);
(Continued)

(58) Field of Classification Search
CPC ...................................................... A61F 2/915
See application file for complete search history.

(56) References Cited

U.S. PATENT DOCUMENTS 5,876,449 A * 3/1999 Starck ................... A61F 2/91
 623/23.7
6,099,561 A * 8/2000 Alt ........................ A61F 2/91
 623/1.34

(Continued)

FOREIGN PATENT DOCUMENTS

CN  1087549 A   6/1994
CN  2577878 Y  10/2003
(Continued)

OTHER PUBLICATIONS

International Search Report and Written Opinion dated Mar. 7, 2016 for International PCT Patent Application No. CN-2015081216.
(Continued)

*Primary Examiner* — Rebecca S Preston
(74) *Attorney, Agent, or Firm* — Schwegman Lundberg & Woessner, P.A.

(57) ABSTRACT

Disclosed herein is a close-cell structured stent which is composed of curved struts that intersect at a crossing angle of 90 to 170 degrees in the longitudinal direction. Methods for making the stent, use of the stent as a vascular stent, an esophagus stent, an intestine stent, a bile conduct stent, or a urinary tract stent, and use of the stent in the manufacture of stent graft for the treatment of abdominal aortic aneurysms are also provided. The stent has both excellent longitudinal flexibility and radial strength.

12 Claims, 3 Drawing Sheets

(51) Int. Cl.
  *A61F 2/07* (2013.01)
  *A61F 2/91* (2013.01)
  *A61F 2/04* (2013.01)

(52) U.S. Cl.
  CPC ......... *A61F 2/042* (2013.01); *A61F 2002/041* (2013.01); *A61F 2002/044* (2013.01); *A61F 2002/075* (2013.01); *A61F 2002/91575* (2013.01); *A61F 2210/0004* (2013.01); *A61F 2210/0014* (2013.01); *A61F 2230/0006* (2013.01); *A61F 2230/0019* (2013.01); *A61F 2230/0021* (2013.01); *A61F 2230/0023* (2013.01); *A61F 2250/0067* (2013.01); *A61F 2250/0098* (2013.01)

(56) References Cited

U.S. PATENT DOCUMENTS

| | | | | |
|---|---|---|---|---|
| 7,491,227 | B2* | 2/2009 | Yang | A61F 2/91 623/1.15 |
| 7,811,314 | B2* | 10/2010 | Fierens | A61F 2/07 623/1.15 |
| 8,172,897 | B2 | 5/2012 | Gale et al. | |
| 9,072,537 | B2 | 7/2015 | Grandfield et al. | |
| 9,687,367 | B2 | 6/2017 | Gill et al. | |
| 2002/0042648 | A1* | 4/2002 | Schaldach | A61F 2/91 623/1.15 |
| 2008/0275537 | A1* | 11/2008 | Limon | A61F 2/91 623/1.15 |
| 2010/0268327 | A1* | 10/2010 | Bruszewski | A61F 2/07 623/1.18 |
| 2010/0330144 | A1 | 12/2010 | Liu et al. | |
| 2012/0215250 | A1 | 8/2012 | Grandfield et al. | |
| 2015/0039019 | A1 | 2/2015 | Cragg et al. | |
| 2015/0080937 | A1 | 3/2015 | Davidson | |
| 2015/0290003 | A1* | 10/2015 | Fischer | A61F 2/91 623/23.7 |
| 2017/0265878 | A1 | 9/2017 | Marchand et al. | |

FOREIGN PATENT DOCUMENTS

| | | |
|---|---|---|
| CN | 1455657 A | 11/2003 |
| CN | 101259045 A | 9/2008 |
| CN | 101621974 A | 1/2010 |
| CN | 102149859 A | 8/2011 |
| EP | 3307211 | 4/2018 |
| WO | WO-99/44543 A1 | 9/1999 |
| WO | WO-01/26583 A1 | 4/2001 |
| WO | WO-2014134568 A2 | 9/2014 |
| WO | WO-2014134568 A3 | 5/2016 |
| WO | WO-2016197351 A1 | 12/2016 |

OTHER PUBLICATIONS

"European Application Serial No. 15894621.0, Extended European Search Report dated Jun. 21, 2018", 8 pgs.

"International Application Serial No. PCT/CN2015/081216, International Preliminary Report on Patentability dated Dec. 21, 2017", 8 pgs.

"European Application Serial No. 15894621.0, Response filed Jan. 4, 2019 to Extended European Search Report dated Jun. 21, 2018", 15 pgs.

* cited by examiner

CLOSE-CELL STRUCTURED STENT, A PREPARATION METHOD AND USE THEREOF

CROSS-REFERENCE

This application is a continuation of International Patent Application No. PCT/CN2015/081216, filed Jun. 11, 2015, the entire content of which is incorporated herein by reference.

TECHNICAL FIELD

The present invention belongs to the field of medical materials and devices, and describes a close-cell structured stent with both excellent longitudinal flexibility and radial strength, and its preparation method and use thereof.

BACKGROUND ART

The use of stent to keep open a blood vessel or other body lumen in the human body has become a very effective therapy for treating blood vessel stenosis and lumen obstruction. For example, using one or more stents to treat a coronary or peripheral artery blockage has become a common practice. Stents have been successfully used in keeping passageways open such as the diseased prostate, urethral, the esophagus, the biliary tract, and intestines. There are two types of stents that are widely used and/or studied nowadays: metallic stents and bioabsorbable polymeric stents.

Flexibility of the stent is one of its important characteristics. A stent has to be flexible in their crimped state in order to facilitate its delivery to a targeted lesion, within an artery. In some cases, a stent also has to be flexible in its deployed and expanded state, especially when implanted in a location where the stent is subjected to flexing or bending, axial compressions and repeated displacements at points along its length. This can produce severe strain and fatigue, resulting in failure of the stent.

Various fabrication methods, such as laser cutting, braiding, and thermal forming have been used to produce stents with various structure designs. Once a material is chosen, the mechanical properties of the stents are largely determined by the stent design structures, including the patterns in which the struts and bridges of the stents are linked together.

One of the primary goals of stent designs has been to insure that the stents have sufficient radial strength so that, when it is delivered to the intended treatment location and expanded, they can sufficiently support the lumen. Stents with high radial strength, however, tend to have a higher longitudinal rigidity or lower flexibility. When a stent has a higher longitudinal rigidity than the vessel in which it is deployed, there is a higher chance that the rigid stent will cause trauma to the vessel at the ends of the stent, due to the stress concentration caused by a mismatch in compliances between the stented and un-stented sections of the vessel. Furthermore, when deployed in certain applications that are subjected to substantial flexing or bending, axial compressions and repeated displacements at points along its length, for example, when stenting the superficial femoral artery, longitudinally rigid or less flexible stent can undergo severe strain and fatigue, resulting in fracture or failure of the stent.

Another important aspect of a stent is its capability to be crimped and then expanded without damaging its structure integrity. Stent structure played a vital role in its structure integrity after expansion.

SUMMARY OF THE INVENTION

One object of the present invention is to provide a novel stent with both excellent longitudinal flexibility and radial strength.

Another object of the present invention is to provide methods for preparing the above mentioned stent.

Yet another object of the present invention is to provide uses of the above mentioned stent.

The objects of the present invention have been achieved by providing the following technical solutions.

In one aspect, the present invention provides a close-cell structured stent which is composed of curved struts that intersect at a crossing angle of from 90 to 170 degrees, preferably from 140 to 150 degrees, in the longitudinal direction.

Preferably, the curvature of curved struts is determined by the distance (d) deviated from its straight line form, and the value of d is preferably in the range of 0.01 mm to 0.99 mm.

Preferably, the stent of the present invention has 4 to 11 crests in the circumferential direction. More preferably, the stent of the present invention is a three dimensional tubular stent.

Preferably, the struts in the stent of the present invention have constant diameters or different diameters; more preferably, the diameters of the struts are from about 50 μm to about 2 mm, most preferably, the diameters of the struts are from 80 μm to 500 μm.

Preferably, the cross section of the struts is a circle, a triangle, a square, a rectangle, a star, or an irregular shape.

Preferably, the stent is mounted on either balloon expandable or self-expanding delivery catheter to form a complete stent system.

Preferably, the stent is made of a non-biodegradable material, a biodegradable material, or a combination thereof; more preferably, the material of the stent is a metal or a polymer; most preferably, the material of the stent is bioresorbable.

Preferably, the stent further contains at least one therapeutic agent.

Preferably, the struts comprise a metal, an inorganic or a polymer composite.

Preferably, the stent has a coating on the surface of the struts. More preferably, the coating is a biodegradable polymer or a non-biodegradable polymer. Most preferably, the coating is composed of a biodegradable polymer and at least one therapeutic agent, or the coating is composed of a non-biodegradable polymer and at least one therapeutic agent.

Preferably, the stent has fabrics attached either to the outer surface or the inner surface or to both surfaces of the stent. More preferably, the fabrics are either woven or non-woven fabrics. Most preferably, the fabrics are either prefabricated or in situ fabricated on the outer surface of the stent. A method for in situ fabrication is an electrospinning fabrication method.

Preferably, small holes are made near the ends or in the middle of the stent to hold radio opaque markers. More preferably, radio opaque materials such as gold or platinum in the forms of beads or powders can be pressed or glued by an adhesive into the marker holes. The adhesive can be a commercially available medical-grade adhesive such as silicone and cyanoacrylates. Most preferably, the adhesive is a polymer solution made of a polymer such as polyvinyl alcohol, polyethylene glycol, polyurethane, polystyrene, polyvinyl polypyrrolidone, poly(L-lactide), poly(D/L-lactide), or polylysine, dissolved in a solvent.

In another aspect, the present invention provides a method for preparing a stent of the present invention, wherein a stent laser cut system is used, and the method comprises the steps of: directing a focused laser beam to the surface of a pre-fabricated thin wall tubing and moving the focused laser beam in a specifically planned path to remove undesired materials so as to obtain a stent of the present invention.

In another aspect, the present invention provides a method for preparing a stent of the present invention, wherein an apparatus for manufacturing a three-dimensional tubular scaffold is used, the apparatus comprising:
 (i) a three-axis XYZ system connected to a base;
 (ii) a dispensing system connected to the XYZ system;
 (iii) a nozzle connected to the dispensing system; and
 (iv) a fourth axis system comprising a rotary rod connected to the base under the nozzle, wherein the nozzle and/or the rotary rod is movable along the axial direction of the rotary rod; and the method comprises the steps of:
  (1) adding raw materials of the stent into the dispensing system of the apparatus; and
  (2) dispensing the materials through the nozzle onto the rotary rod.

In another aspect, the present invention provides use of a stent of the present invention as a vascular stent, an esophagus stent, an intestine stent, a bile conduct stent, or a urinary tract stent.

In yet another aspect, the present invention provides use of a stent of the present invention in the manufacture of a stent graft for the treatment of abdominal aortic aneurysms.

The stent of the present invention has both excellent longitudinal flexibility and radial strength. The inventors of the present invention have surprisingly discovered that the fiber cross angle in the longitudinal direction (θ) has important influence on the stent structure and mechanical property, and when the fiber cross angle in the longitudinal direction (θ) ranges from 90° to 170°, the stent has desirable radial strength and stent shortening ratio, and could be easily crimped and then expanded without damaging its structure integrity. The inventors of the present invention have also surprisingly discovered that the stent with curved fiber struts has much greater radial strength than the stent with non-curved fiber struts. Additionally, the stents with curved struts are stronger than those with straight struts.

BRIEF DESCRIPTION OF THE DRAWINGS

A full and enabling disclosure of the present invention is set forth more particularly in the remainder of the specification, including reference to the accompanying figures, in which.

BEST MODE FOR CARRYING OUT THE INVENTION

Unless otherwise specified, the terms used in the specification and claims of the instant application are defined as follows.

The term "a crossing angle in the longitudinal direction" as used herein refers to an angle which is determined by two intersected straight lines that connect 3 neighboring intersecting points in the longitudinal direction of curved struts forming one crest of the stent of the present invention such as points C, D, and E as shown in FIG. 1B.

The term "crest(s)" as used herein refers to peak(s) in the stent of the present invention such as those shown in the structure of the stents.

The term "ring(s)" as used herein refers to the ring(s) formed by the stent-constituting material going around the periphery of the stents.

A close-cell structured stent which is composed of curved struts that intersect at a crossing angle of 90 to 170 degrees in the longitudinal direction is provided.

Figure 1:
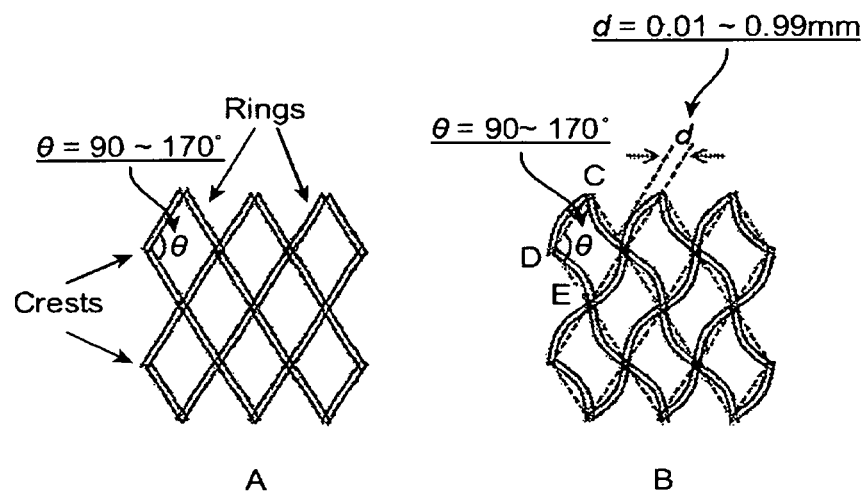
FIG. 1 representatively illustrates two-dimensional drawing of stent design elements consisting of straight (A) and curved (B) struts intersect at a particular range of crossing angles in the longitudinal direction (θ).

FIG. 1 representatively illustrates two-dimensional drawing of close-cell structured stent design elements consisting of straight (A) and curved (B) struts intersect at a particular range of crossing angles in the longitudinal direction (θ), which is determined by the two intersected straight lines that connect the 3 neighboring intersecting points in the longitudinal direction of curved struts forming one crest of the stent (points C, D and E, as shown in FIG. 1B), ranging from 90 to 170 degrees. The curvature of curved struts can be determined by the distance (d) deviated from its straight line form. The value of d is preferably in the range of 0.01 mm to 0.99 mm.

Figure 2:
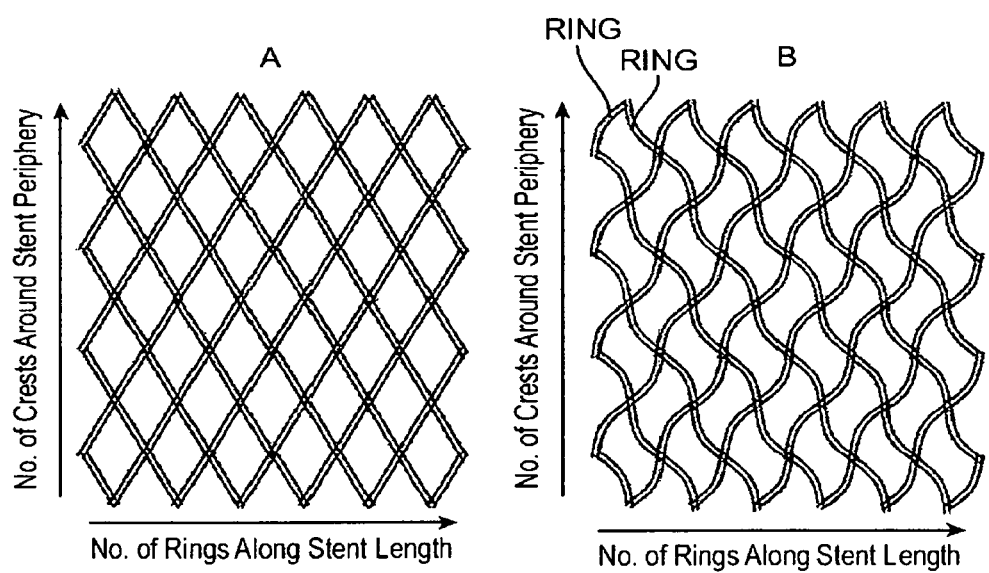
FIG. 2 representatively illustrates two-dimensional drawing of stent segments consisting of straight (A) and curved (B) fibers.

In FIG. 2, two-dimensional drawing of stent segments consisting of straight (A) and curved (B) fibers crossing by 4 crests (or peaks) around the stent periphery and 12 rings along the stent length are representatively illustrated.

Figure 3:
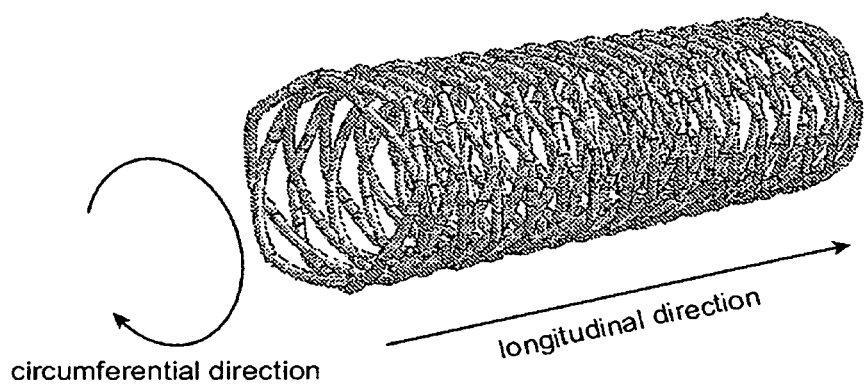
FIG. 3 representatively illustrates a three-dimensional view of an embodiment of the stent of the present invention with struts intersect at a crossing angle in the longitudinal direction of 145°.

In FIG. 3, a three-dimensional view of an embodiment of the stent of the present invention with struts intersect at a crossing angle in the longitudinal direction of 145° is representatively illustrated.

Figure 4:
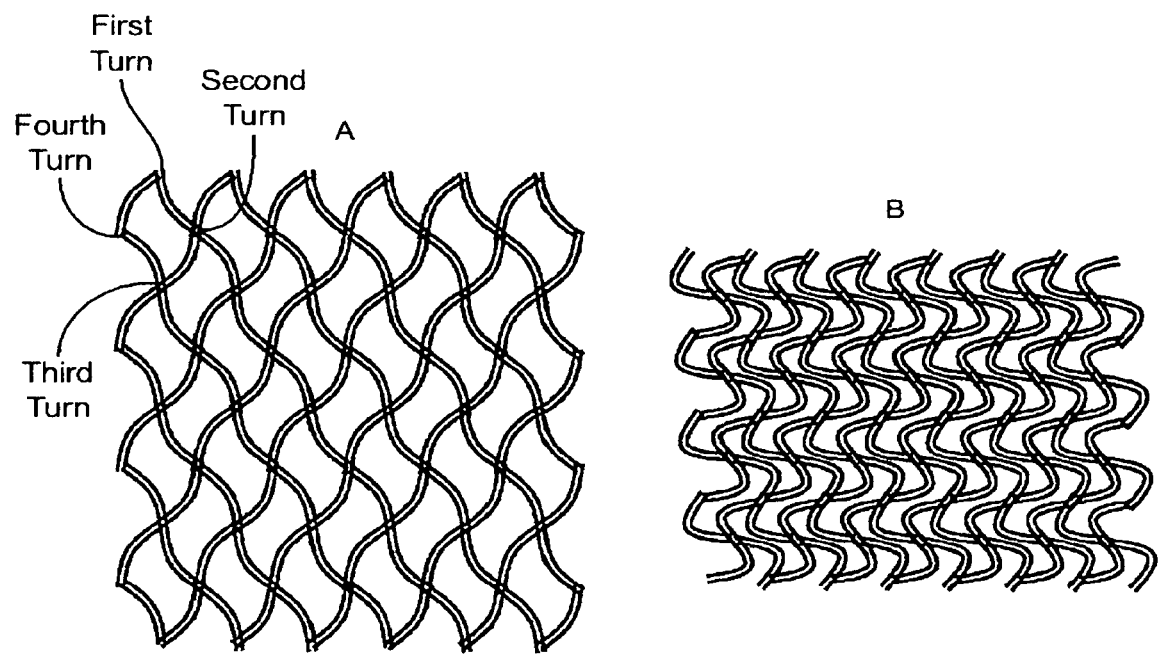
FIG. 4 is a demonstration of an embodiment of the stent of the present invention in its expanded (A) and crimped (B) forms.

As shown in FIG. 4, the close-cell structured stent with curved struts of the present invention has little or no changes in its longitudinal length in its expanded (A) and crimped (B) forms. The curvature of the struts will allow or guide the deformation of the struts during the crimping process so that the overall longitudinal expansion is minimized. The crimping allows the stent to be mounted on conventional balloon catheters used for transluminal stent delivery. FIG. 4A also shows the first turn, the second turn, the third turn, and the fourth turn between adjacent struts in a closed cell.

In certain embodiments, the present invention is directed to a 3D tubular stent comprising connected struts to form a porous three-dimensional pattern, the stent having an average pore size from about 1 to about 10000 microns.

In further embodiment, the stents comprise struts connected in a pre-designed three-dimensional pattern.

The stent of the present invention may be made of a non-biodegradable material, a biodegradable material, or a combination thereof.

Non-biodegradable material for use in the present invention include, for example, metals, e.g. stainless steel, metal alloys of nickel and titanium (Nitinol materials), non-degradable synthetic polymers, e.g. polyethylene terephthalate, polyamide, polyurethane, etc. and composites thereof.

Biodegradable materials for use in the present invention include, but not limited to, magnesium alloy, polylactic acid (PLA), polyglycolic acid (PGA), polycaprolactone (PCL), polyanhydrides, poly(β-hydroxybutyrate), polydioxanone, poly(DTH iminocarbonate), polypropylene fumarate, etc. copolymers thereof and mixtures thereof.

The stent of the present invention may be configured in any size to accomplish the particular purpose at hand, e.g., size suitable for use in coronary, periphery, abdomen aorta, urinary track, esophagus, bile duct, GI track, etc.

The struts of the stents may have constant diameters or different diameters. In preferred embodiments, the diameter of the struts of the stent are from about 50 um to 2 mm, more preferably the diameters of the struts are from 80 μm to 500 μm.

The cross sections of the struts may be a circle, a triangle, a square, a rectangle, a star, or an irregular shape.

The surface of the stents may also be treated by coating means, in which a substance is applied on the surface that is different from the material of the struts. The substance can be covalently bonded or physically absorbed to the surface of the struts. Alternatively, the substance can be bonded to the surface of the construct through hydrogen bonding, ionic bonding, Van der Waals force or a combination thereof. To increase the stability of the biological molecular coating, the coating can be crosslinked using various crosslinking technologies, such as chemical crosslinking, radiation, thermal treatment, or a combination thereof, etc. Further, the crosslinking can take place in a vacuum at an elevated temperature above room temperature. The radiation used for crosslinking can be e-beam radiation, gamma radiation, ultraviolet radiation, or a combination thereof.

The coating substance can be a mixture of polymers and therapeutic agents.

The coating substance can be a protein, peptide, glycoaminoglycan, a naturally occurring substance, an inorganic substance, a therapeutic agent, or a combination thereof.

The surface of the stents can be further coated with biological molecules or naturally occurring compound or polymer, such as, but not limited to, collagen (type I, II, III, IV, V, IV, etc), fibronectin, laminin, or other extracellular matrix molecules. Examples of extracellular matrix molecules are heparan sulfate, chondroitin sulfate, keratan sulfates, hyaluronic acid, elastin, hemicellulose, pectin, and extensin. The biological molecules are either covalently bonded to the surface, or physically absorbed to the surface of the tubular stents.

The surface of the stents can be further surface coated with a synthetic polymer, such as, polyvinyl alcohol, polyethylene glycol, polyvinyl polypyrrolidone, poly(L-lactide), polylysine, etc.

The surface of the stents can also be coated with organic substance, such as gelatin, chitosan, polyacrylic acid, polyethylene glycol, polyvinyl alcohol, polyvinylpyrrilidone or a combination thereof.

Alternatively, the stents may be coated with an inorganic material, such as calcium phosphate, $TiO_2$, $Al_2O_3$, or a combination thereof.

In a specific embodiment, the stents are coated with a composite coating of two or more organic materials, such as, gelatin and chitosan, polyacrylic acid and polyethylene glycol, polyvinyl alcohol and polyvinylpyrilidone, etc.

The stents may also be coated with a composite coating of a combination of inorganic and organic materials, such as, calcium phosphate/collagen, calcium phosphate/gelatin, calcium phosphate/polyethylene glycol, etc.

The stents of the present invention may also be used together with fabrics. The fabrics can be attached either to the outer surface or the inner surface or to both surfaces of the stents via any means that is known in the art, such as heating, ultra sound welding, adhesive, suture, etc.

The fabrics for attaching to the stent can be either woven or non-woven fabrics or both, or the fabrics for attaching to the stent can be either bio-absorbable or non-bioabsorbable fabrics or both.

The fabrics can be prefabricated or in situ fabricated on the outer surface of the stent. The in situ fabrication method included, but not limit to, an electrospinning fabrication method in which the rotation shaft with the stents still on serves as the fiber collector.

Figure 5:
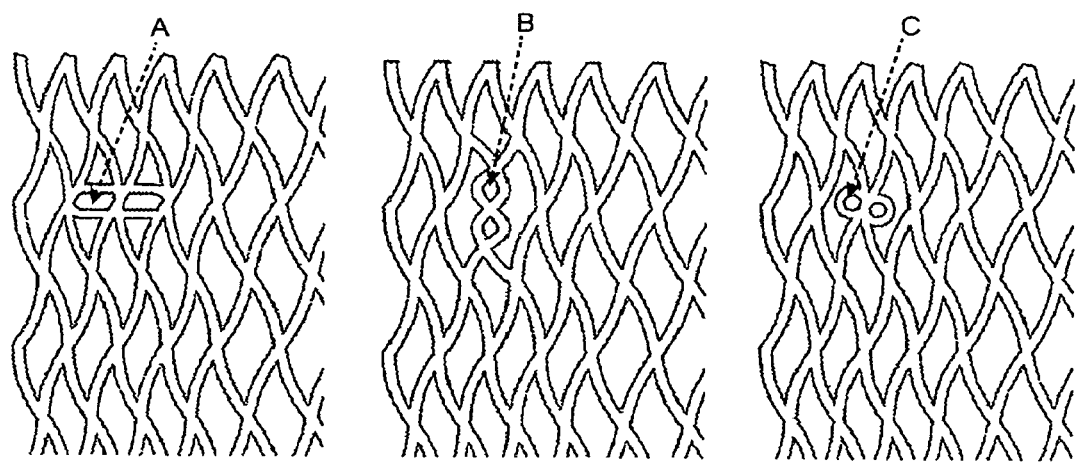
FIG. 5 is an illustration of three types of stent marker holes (A, B and C) designed for housing x-ray visible markers.

To improve the visualization of the stents under x-ray, small radio opaque markers can be placed on the stents. Small marker holes are made on the stent either near each end or in the middle of the stent to house the radio opaque markers usually made of biocompatible metallic materials such as gold or platinum in the forms of beads or powders (FIG. 5).

The gold or platinum beads or powders in a size range of 0.005 mm to 0.5 mm can be pressed or glued by an adhesive into the marker holes. The adhesive can be a commercially available medical-grade adhesive such as silicone and cyanoacrylates. The adhesive can also be made from a polymer solution made of a polymer such as polyvinyl alcohol, polyethylene glycol, polyurethane, polystyrene, polyvinyl polypyrrolidone, poly(L-lactide), poly(D/L-lactide), polylysine, etc., dissolved in a solvent.

The Apparatus and Methods for Manufacturing a Stent

The close-cell structured stent of the present invention can be manufactured by a laser cutting system which has been widely used in producing metallic stents and polymeric stents. When using a laser cut system to produce said close-cell structured stent, a pre-fabricated thin wall tubing, either metallic or polymeric, was used. A focused laser beam is directed to the surface of the tubing and moves in a specifically planned path to remove the undesired material so that a stent with said close-cell structure is formed.

Another method to produce a stent is to use a 4-axis rapid polymer (RP) stent fabricating apparatus which was disclosed in U.S. Patent Application Publication No. 2010/0330144A1. The 4-axis RP stent fabrication apparatus is an apparatus for manufacturing a three-dimensional tubular scaffold comprising:
  (i) a three-axis XYZ system connected to a base;
  (ii) a dispensing system connected to the XYZ system;
  (iii) a nozzle connected to the dispensing system; and
  (iv) a fourth axis system comprising a rotary rod connected to the base under the nozzle, wherein the nozzle and/or the rotary rod is movable along the axial direction of the rotary rod.

The $4^{th}$ axis of the aforesaid 4-axis rapid polymer (RP) stent fabricating apparatus is preferably a computer controlled rotation shaft added to a xyz position system. More preferably, the 4-axis RP apparatus also has two or more material delivery systems that deposit material in a hot melt filament form or a viscous solution filament form in a sequential order.

The deposited filament adheres to the surface of the rotation shaft or bonds to previously extruded filaments that already attached to the rotation shaft, therefore eliminating the need to use glue or controlled heating. In addition, the fiber diameter can be controlled by either varying the rotation speed of the 4th axis where the filament is attached, or by varying the XY axis traveling speed, similar to a hot melt drawing process.

Applications of the Stents

The stents of the present invention may be used as vascular stents, which are delivered by transcutaneous catheters to a plagued and narrowed segment of a blood vessel, the stent will keep the blood vessel open for easy blood flow.

The stents of the said invention can be mounted on either balloon expandable or self-expanding delivery catheters similar to the currently used balloon expandable or self-expanding stents.

The stents of the present invention may be used as esophagus stents, which, when placed and expanded in a narrowed segment of an esophagus, will keep the esophagus open for easy food flow into stomach. Such an application will be advantageous for late stage esophagus cancer patients.

Similarly, the stents of the present invention may also be used as stents designed for the intestines, the bile conduct, urinary tract, etc.

The stents of the present invention may also be used further to make stent graft for treatment of abdominal aortic aneurysms.

EXAMPLES OF THE STENTS

Example 1—Manufacturing of Peripheral Stents

Using the 4-axis rapid polymer (RP) stent fabricating apparatus as described in U.S. Patent Application Publication No. 2010/0330144A1, stents with curved fiber struts (d=0.16 mm) and non-curved fiber struts and with fiber crossing angles in the longitudinal direction of 90, 140, 145 and 150 degrees were made from poly(L-lactic acid), i.e., PLLA, in sizes of 5 mm in diameter and 36 mm in length. The stents were then crimped onto 5 mm×40 mm×85 cm balloon catheters using the Blockwise Model RJX stent crimping machine set at a final diameter of 2.35 mm. The stents were then expanded by balloon inflation in a water bath at 37 C. The expanded stents were used for the measurement of radial forces using the Blockwise Model TTR2 radial force tester. The results were shown in Table 1.

TABLE 1

| Fiber Cross Angle in the Longitudinal Direction (θ, degree) | Number of Crests Around Stent Periphery | Number of Fiber Rings Along Stent Length | Average Radial Strength (N/mm) | Average Stent Shortening Ratio (%) |
|---|---|---|---|---|
| 90° | 11 | 50 | 0.81 (non-curved) | 28.6 |
| 140° | 4 | 50 | 1.22 (curved) | 8.9 |
| 145° | 4 | 57 | 1.43 (curved) 1.16 (non-curved) | 9.4 |
| 150° | 4 | 71 | 2.10 (curved) 1.35 (non-curved) | 11.3 |

For peripheral stents, the fiber cross angle in the longitudinal direction (θ) has important influence on the stent structure and mechanical property. Within θ values of 140° and 150°, the number of crests around stent periphery is 4, whereas the number of crests around stent periphery is increased to 11 when the fiber cross angle in the longitudinal direction (θ) is decreased to 90°. From 140° to 150°, the greater the fiber cross angle in the longitudinal direction is, the more fiber rings along stent length are. The stent radial strength also increases with increasing θ. The stent shortening ratio at 90° is the highest among those at 140°, 145° and 150° (almost 3 times as much). When the fiber cross angle is further decreased to an angel smaller than 90, the stent shortening ratio becomes too high and is not desirable in clinical applications. On the other hands, when the angle becomes higher than 170, crimping of the stents becomes difficult and the stent shortening ratio will increase to a high level that is not desirable clinically. It was also surprisingly discovered that the stent with curved fiber struts has much greater radial strength than the stent with non-curved fiber struts. Additionally, the stents with curved struts are stronger than those with straight struts, as the curvature of the struts will guide the direction of the strut deformation during a crimping process. On the contrary, the stents with non-curved struts (straight struts) deform in a non-controlled way which leads to crack formation in overly deformed region.

Example 2—Manufacturing of Coronary Stents

Using the 4-axis rapid polymer (RP) stent fabricating apparatus as described in U.S. Patent Application Publication No. 2010/0330144A1, stents with curved fiber struts (d=0.16 mm) and with fiber crossing angles in the longitudinal direction of 141, 145 and 150 degrees were made from poly(L-lactic acid), i.e., PLLA, in size of 3 mm in diameter and 13 mm in length. The stents were then crimped onto 3 mm×15 mm×135 cm balloon catheters using a Blockwise Model RJX stent crimping machine set at a final diameter of 1.45 mm. The stents were then expanded by balloon inflation in a 37° C. water bath. The expanded stents were then used for the measurement of radial forces using the Blockwise Model TTR2 radial force tester. The results were shown in Table 2.

TABLE 2

| Fiber Cross Angle in the Longitudinal Direction (θ, degree) | Number of Crests Around Stent Periphery | Number of Fiber Rings Along Stent Length | Average Radial Strength (N/mm) | Average Stent Shortening Ratio (%) |
|---|---|---|---|---|
| 141° | 4 | 29 | 1.66 | 5.9 |
| 145° | 4 | 33 | 1.83 | 7.9 |
| 150° | 4 | 37 | 2.02 | 18.1 |

For coronary stents, the fiber cross angle in the longitudinal direction (θ) plays an important role in the stent structure and mechanical property. The stent radial strength increases with increasing θ. The stent shortening ratio at 150° θ is markedly higher than those at 141° and 145°.

What is claimed is:

1. A stent comprising:
a plurality of circumferentially oriented struts coupled together to form a plurality of closed rings, wherein adjacent closed rings are coupled together to form a plurality of closed cells, wherein each closed cell consists of four curved struts coupled together, the four curved struts each having a first end and a second end opposite the first end, wherein a straight line extends from the first end to the second end,
wherein the four curved struts consist of a first curved strut consisting of a first curved region, a second curved strut consisting of a second curved region, a third curved strut consisting of a third curved region, and a fourth curved strut consisting of a fourth curved region, wherein an inner portion of the first curved region consists of a first concave region facing inward toward a center of a first closed cell, wherein an outer portion of the second curved region consists of a second concave region facing outward away from the center of the first closed cell, wherein an inner portion of the third curved region consists of a third concave region facing inward toward the center of the first closed cell, and wherein an outer portion of the fourth curved region consists of a fourth concave region facing outward away from the center of the first closed cell, wherein the first curved strut, the second curved strut, the third curved strut, and the fourth curved strut are arranged in a clockwise pattern with the first curved strut following the fourth curved strut, the second curved strut following the first curved strut, the third curved strut following the second curved strut, and the fourth curved strut following the third curved strut, wherein one end of the first curved strut is coupled to one end of the second curved strut to form a first turn in the closed cell, and an opposite end of the second curved strut is coupled to one end of the third curved strut to form second turn in the closed cell, and an opposite end of the third curved strut is coupled to one end of the fourth curved strut to form a third turn in the closed cell, and an opposite end of the fourth curved strut is coupled to an opposite end of the first curved strut to form a fourth turn in the closed cell, and wherein the first turn, the second turn, the third turn, and the fourth turn exist when the plurality of rings are in a crimped form, wherein at least some of the four curved struts intersect one another at an angle from 90 to 170 degrees in a longitudinal direction, and wherein a radial strength of the stent increases when the angle increases, and wherein the first curved region, the second curved region, the third curved region, and the fourth curved region deform and guide deformation of the plurality of circumferentially oriented struts during crimping of the stent into the crimped form and with minimal longitudinal expansion of the stent.

2. The stent of claim 1, wherein the first curved strut has an outer portion with only a first convex region facing outward away from the center of the first closed cell,
wherein the second curved strut has an inner portion with only a second convex region facing inward toward the center of the first closed cell,
wherein the third curved strut has an outer portion with only a third convex region facing outward away from the center of the first closed cell, and
wherein the fourth curved strut has an inner portion with only a fourth convex region facing inward toward the center of the first closed cell.

3. The stent of claim 1, wherein the angle is from 140 to 150 degrees.

4. The stent of claim 1, wherein a curvature of the four curved struts is defined by a deviation of the four curved struts a distance d from the straight line, and wherein d is in the range of 0.01 mm to 0.99 mm.

5. The stent of claim 1, wherein at least some of the four curved struts have a cross-section, the cross-section being a circle, a triangle, a square, a rectangle, a star, or an irregular shape.

6. The stent of claim 1, wherein the stent is formed from a biodegradable material or a non-biodegradable material.

7. The stent of claim 1, further comprising a therapeutic agent carried by the at least some of the plurality of rings.

8. The stent of claim 1, further comprising a coating disposed on the at least some of the four curved struts.

9. The stent of claim 1, further comprising a fabric coupled to at least some of the four curved struts.

10. The stent of claim 1, further comprising a plurality of radiopaque markers coupled to at least some of the four curved struts.

11. The stent of claim 1, wherein the first curved strut is coupled directly to the second curved strut, the second curved strut is coupled directly to the third curved strut, the third curved strut is coupled directly to the fourth curved strut, and the fourth curved strut is coupled directly to the first curved strut.

12. The stent of claim 1, wherein each closed cell has a first dimension in a circumferential direction and a second dimension extending along a longitudinal axis of the stent, and wherein the first dimension is larger than the second dimension in an expanded configuration.

* * * * *

UNITED STATES PATENT AND TRADEMARK OFFICE
CERTIFICATE OF CORRECTION

PATENT NO. : 10,603,194 B2
APPLICATION NO. : 15/837445
DATED : March 31, 2020
INVENTOR(S) : Zhao et al.

Page 1 of 1

It is certified that error appears in the above-identified patent and that said Letters Patent is hereby corrected as shown below:

In the Specification

In Column 5, Line 60, delete "Al$_2$0$_3$," and insert --Al$_2$O$_3$,-- therefor In the Claims In Column 9, Line 37, in Claim 1, delete "90to" and insert --90 to-- therefor Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*